United States Patent [19]

Hawthorne

[11] 4,099,329
[45] Jul. 11, 1978

[54] ARCH FORMS AND A METHOD OF MOULDING SAME

[75] Inventor: Horace Stanley Hawthorne, West Midlands, England

[73] Assignee: Lucas Electrical Limited, Birmingham, England

[21] Appl. No.: 679,071

[22] Filed: Apr. 21, 1976

[51] Int. Cl.² ............................................ A61C 19/00
[52] U.S. Cl. ............................................. 32/2; 32/11
[58] Field of Search ................................. 32/2, 8, 11

[56] References Cited

U.S. PATENT DOCUMENTS

| 2,778,110 | 1/1957 | Gooris | 32/2 |
| 3,644,996 | 2/1972 | Weinkle | 32/2 |
| 3,838,513 | 10/1974 | Katz | 32/2 |
| 3,839,796 | 10/1974 | Hazar | 32/2 |

*Primary Examiner*—Robert Peshock
*Attorney, Agent, or Firm*—Holman & Stern

[57] ABSTRACT

An arch form comprises a tooth portion including a plurality of integral teeth injection moulded in pastics material and arranged in a curved row, and a gum portion in situ injection moulded onto the tooth portion so as to overlie an upper surface thereof. An undulating ridge extends along the upper surface of the tooth portion and is surrounded by the gum portion. Front teeth of the tooth portion have a substantially natural inclination with respect to the general plane of the tooth portion, whereas rear teeth thereof are inclined towards the front teeth such that their direction of extent is angled at 10° to 20° with respect to their counterparts in a natural set of teeth.

A method of moulding the arch form requires the provision of a two-part mould defining the shape of the tooth portion, and a further mould part defining the shape of the gum portion. One part of the two-part mould includes a curved row of interconnected cavities defining the shapes of the individual teeth of the tooth portion: the other part thereof defines the upper surface of the tooth portion and the undulating ridge. Substantially white plastics material is injected into the two-part mould so as to form the tooth portion. The said other part of the two-part mould is then removed and is replaced by the further mould part. Red or pink plastics material is then injection into further mould part so as to mould the gum portion in situ on the tooth portion. The further mould part is withdrawn, and the completed arch form is removed.

The arch form can be produced in an economic manner and in a form which facilitates mass production.

9 Claims, 9 Drawing Figures

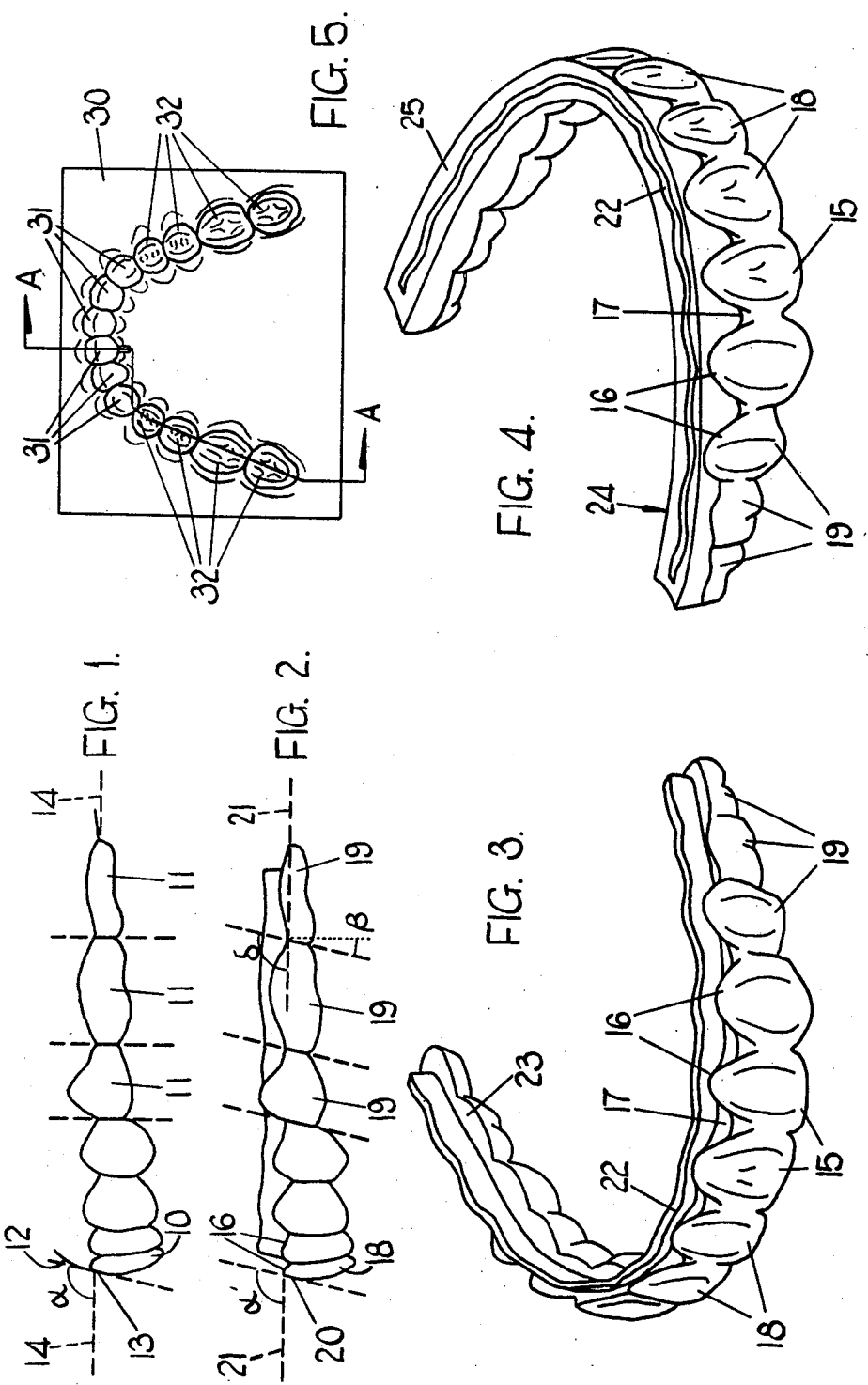

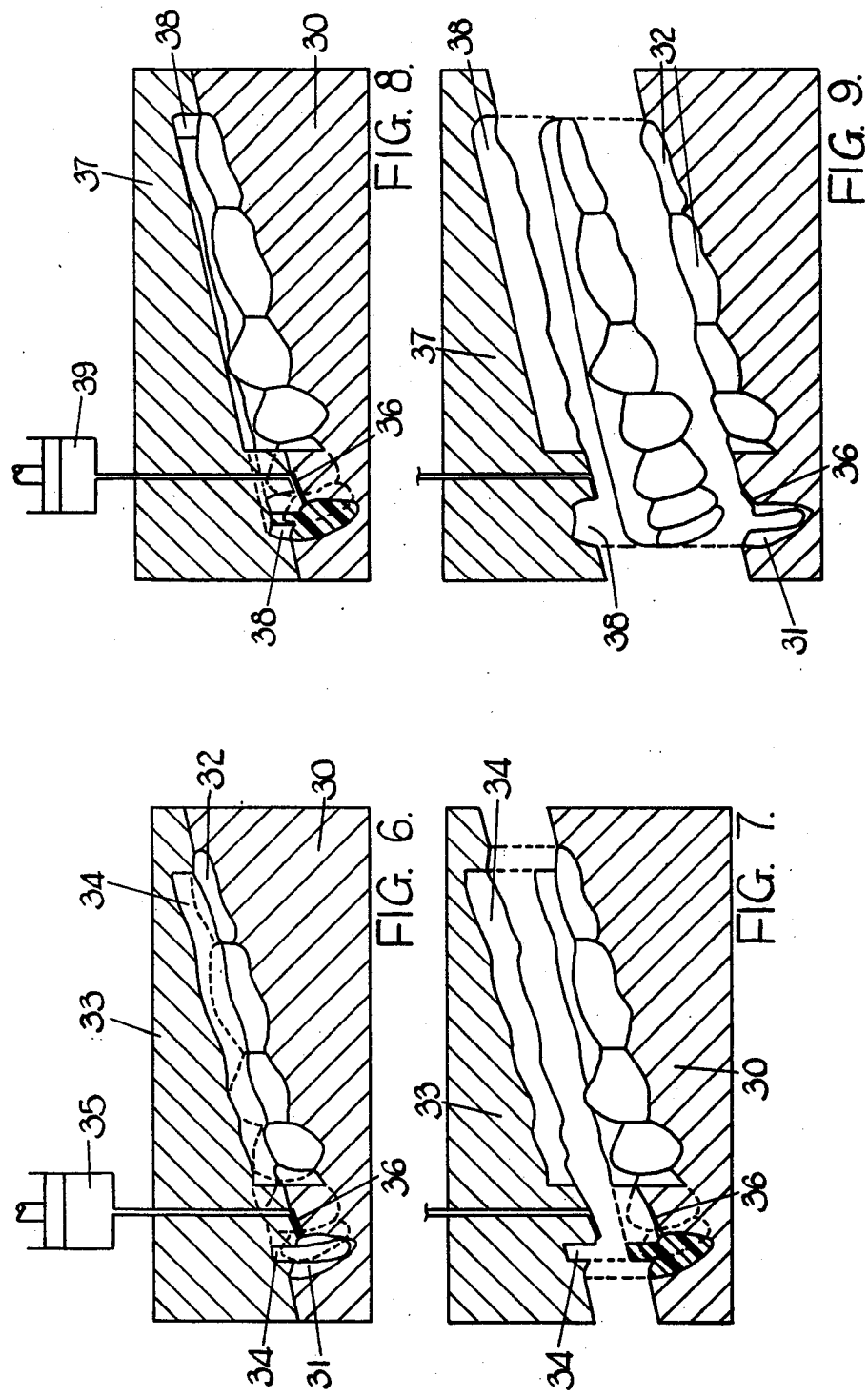

ARCH FORMS AND A METHOD OF MOULDING SAME

This invention relates to arch forms and a method of moulding same, and has as its object the production of a denture in an economic manner and in a form which facilitates mass production thereof.

According to the present invention, there is provided an arch form comprising a tooth portion including a plurality of integral teeth injection moulded in a plastics material and arranged in a row in the manner in which they are to appear in the completed arch form, a gum portion in situ injection moulded onto said tooth portion so as to overlie a part thereof, and at least one integral projection provided on said part of said tooth portion, said gum portion surrounding said at least one projection.

Conveniently, front teeth of the tooth portion have a substantially natural inclination with respect to the general plane of the tooth portion, and rear teeth of the tooth portion are inclined towards the front teeth such that their direction of extent is angled with respect to their counterparts in a natural set of teeth, preferably at an angle of between 10° and 20°.

Further according to the present invention, there is provided a method of moulding an arch form comprising the steps of: providing a two-part mould defining the shape of a tooth portion of said arch form, one part of said two-part mould inclining a row of interconnected cavities defining individual teeth of said tooth portion arranged in the manner in which they are to appear in the completed arch form, the other part of said two-part mould defining a part of said tooth portion which is to be covered by a gum portion and also defining at least one projection on said part of said tooth portion; injecting plastics material into said two-part mould thereby forming said tooth portion; withdrawing said other part of said two-part mould from said one part thereof; providing a further mould part defining said gum portion; placing said further mould part over said part of said tooth portion to be covered by said gum portion when said tooth portion is in said one part of said two-part mould or in another mould; injecting plastics material into said further mould part, thereby in situ moulding said gum portion onto said tooth portion so as to overlie said part thereof and surround said at least one projection; withdrawing said further mould part from said one part of said two-part mould or said another mould, as the case may be; and removing the resultant moulded arch form from said one part of said two-part mould or said another mould, as the case may be.

Advantageously, the cavities in the one part of the two-part mould which define rear teeth are inclined towards the cavities which defined front teeth, such that there are no undercut surfaces in the mould with respect to a predetermined direction; and the moulded tooth portion is removed from the one part of the two-part mould in this predetermined direction.

Embodiments of the present invention will now be described, by way of example with reference to the accompanying drawings in which:

FIG. 1 is a side view of a natural set of teeth;

FIG. 2 is a side view of a tooth portion of an arch form according to the present invention;

FIG. 3 is a perspective view of the tooth portion of FIG. 2;

FIG. 4 is a perspective view of an arch form including the tooth portion of FIG. 2;

FIG. 5 is a plan view of one part of a mould used in a method of moulding an arch form, according to the present invention; and FIGS. 6 to 9 are sectional views showing different stages in the method according to the present invention, the sections being taken along the line A—A in FIG. 5.

Referring to FIG. 1, there is shown therein a natural set of teeth having front and rear teeth 10 and 11 respectively projecting from a gum 12. The front teeth 10 project forwardly from the gum 12 such that part 13 of the respective faces thereof adjoining the gum 12 are inclined at an obtuse angle $\alpha$ to a general plane 14 of the teeth taken as a whole. The rear teeth 11 extend in a direction which is substantially perpendicular to the plane 14. As will be seen later, the arch form of the present invention has front teeth which have an inclination similar to that of the teeth 10, but whose rear teeth are angled with respect to the direction of extent of the teeth 11.

Referring to FIGS. 2 to 4, the arch form of the present invention is intended for use in a denture which is a replacement for a full upper or lower set of human teeth, and comprises a tooth portion including a plurality of integral teeth 15 formed by means of an injection moulding process and arranged in a curved row. The teeth 15 are integrally formed with a projection in the form of a ridge 22 whose purpose will be described hereinafter. Each tooth 15 has a ridge 16 thereon defining its base.

The ridges 16 are disposed as an outer edge of the tooth portion, and a fillet 17 is formed integrally between the ridges 16 on each pair of adjacent teeth 15.

The teeth 15 include front teeth 18 and rear teeth 19. As is shown particularly in FIG. 2, the front teeth 18 project forwardly and part 20 of their respective faces which adjoin the respective ridges 16 are inclined at an obtuse angle $\alpha'$ to a general plane 21 of the tooth portion. The angle $\alpha'$ is arranged to be approximately equal to the angle $\alpha$ of the natural teeth shown in FIG. 1, thereby giving the teeth 18 a natural inclination with respect to the plane 21. The rear teeth 19 are slanted towards the front teeth 18, such that their direction of extent is inclined at an angle $\beta$ with respect to their counterpart teeth 11 in the natural set of teeth of FIG. 1, and at an obtuse angle $\delta$ to the general plane 21 of the tooth portion as a whole. The angle $\beta$ is preferably between 10° and 20°, and in this embodiment it is equal to 14°. The latter is an optimum value resulting in the front teeth 18 having a natural inclination and the rear teeth 19 not being unduly inclined. The reason for this inclination of the teeth 19 will become apparent later on.

Referring particularly to FIGS. 3 and 4, the ridge 22 is of undulating form and extends along the row of teeth 15, on a surface 23 thereof adjacent the bases of the teeth 15. A gum portion 24 is in situ moulded on the surface 23 of the tooth portion as to surround the ridge 22. The gum portion 24 has a concave surface 25 remote from the tooth portion and at least part of the ridge 22 is arranged to extend to this surface 25. The ridge 22 thus provides a key for the gum portion 24.

Both the tooth portion and the gum portion 24 are injection moulded using an acrylic plastics material having a high temperature resistance. In an alternative embodiment (not shown), the ridge 22 is provided with a slot or slots therein to ensure proper flow of the plastics material from which the gum portion 24 is formed when the latter is being injection moulded.

Referring now to FIG. 5, there is shown therein a lower mould half 30 used for producing a tooth portion as described above. The mould half 30 has interconnected cavities 31 therein which defined the individual front teeth 18 of the tooth portion, and interconnected cavities 32 which define the individual rear teeth 19. In order that the moulded tooth portion may be removed from the mould half 30 in a predetermined direction, there must be no undercut surfaces in the cavities 31, 32 with respect to that direction. For this reason, the cavities 32 are inclined towards the cavities 31 such that, in the resultant moulded tooth portion, the angle δ is not less than, and is preferably greater than the angle α' (the angle δ is the obtuse angle between the direction of extent of the rear teeth 19 and the general plane 21 of the tooth portion, and the angle α' is the obtuse angle at which the parts 20 of the faces of the front teeth 18 are inclined with respect to the plane 21).

Moulding of the denture commences by placing an upper mould half 33 on top of the lower mould half 30, as shown in FIG. 6. The mould half 33 has a cavity 34 therein which defines the ridge 22 and the surface 23 of the tooth portion. The boundary line between the two mould halves 30 and 33 defines the ridges 16 and fillets 17 on the tooth portion.

Acrylic plastics material having a high temperature resistance and which is substantially white in colour is then injected into the resultant mould by an injection moulding machine 35, illustrated schematically, via a gate 36 disposed at the rear of one of the cavities 31 and substantially midway along the rear of the mould. The injection moulding operation is performed at a temperature of 220° to 250° C and at a pressure of about 20,000 p.s.i.

When the tooth portion has solidified, the upper mould half 33 is withdrawn, as shown in FIG. 7, and is replaced by a further upper mould half 37, as shown in FIG. 8. The mould half 37 has a cavity 38 therein defining the gum portion 24, and the boundary line between the two mould halves 30 and 37 again coincides with the ridges 16 and fillets 17 of the denture.

Red acrylic plastics material having a high temperature resistance is then injected into the cavity 38 by an injection moulding machine 39, illustrated schematically, via the gate 36. The injection operation is performed under the same conditions as above. When the gum portion 24 has solidified, the mould half 37 is withdrawn and the resultant arch form, comprising the tooth portion with the gum portion 24 thereon, is removed from the mould half 30 in the aforementioned determined direction, as shown in FIG. 9.

Thus, by arranging the rear teeth of the tooth portion of the arch form to be inclined towards the front teeth, the tooth portion can be moulded with the front teeth thereof projecting slightly forwardly, as in a natural set of teeth, using a two-part mould. This obviates the requirement for a multi-sectional mould which would otherwise have to be used.

An arch form moulded by the above-described method does not look completely natural per se. Although the front teeth of the tooth portion are inclined at an angle which is not substantially different from that of natural front teeth, the rear teeth are inclined at a different angle from that of their counterpart natural teeth. Nevertheless, when the arch form is incorporated into a denture and is fitted in the mouth, the front teeth are more prominent than the rear teeth, and the inclination of the latter is not readily apparent. Thus the completed denture, when fitted, does give a substantially natural appearance.

Production of the arch form by a two-colour process may be carried out in a cyclic operation. The tooth portion is firstly injection moulded using the upper and lower mould halves 30 and 33 respectively. The upper mould half 33 is then replaced by the further mould half 37, and the gum portion 24 is in situ injection moulded onto the tooth portion. By suitable arrangement of injection machines 35, 39 and mould halves 30, 33 and 37, a cycle time of 45 to 50 seconds can be achieved for this operation.

As an alternative to manufacturing the arch form on a single, two-colour machine, the gum portion can be moulded onto the tooth portion by inserting the previously moulded tooth portion into another mould (not shown). One part of said mould defines the teeth of the tooth portion and is filled by the previously moulded tooth portion, and another part of said mould defines the gum portion. The tooth portion may be preheated in a suitable oven at a temperature of 175° – 185° C for 4–5 minutes prior to being inserted into said mould. The gum portion is then injection moulded onto the preheated tooth portion.

The arch form manufactured as described above can then be used in the production of a denture by bonding it into a gum moulding taken from a patient. The arch form according to the present invention can be conveniently used to produce cheaply a replacement or temporary denture.

I claim:

1. An arch form comprising a tooth portion including a plurality of integral teeth of a first plastics material, each tooth having a base portion, an integral fillet between said base portions at each pair of adjacent teeth, at least one integral projection provided on said tooth portion, and a gum portion of a second plastics material, said second plastics material being of a different color than said first plastics material, and said gum portion surrounding said at least one projection and meeting said tooth portion at least at said fillet.

2. An arch form as claimed in claim 1 wherein said at least one projection is in the form of a ridge extedning over said tooth portion in spaced relationship to said base portions of said teeth.

3. The arch form according to claim 2 wherein said ridge has a part which extends to a surface of said gum portion remote from said teeth.

4. The arch form according to claim 1, wherein said rear teeth are inclined with respect to their said counter parts in a natural set of teeth at an angle of between 10° and 20°.

5. The arch form according to claim 4, wherein said angle is 14°.

6. A method of moulding an arch form comprising the steps of: providing a two-part mould defining the shape of a tooth portion of said arch form, one part of said two-part mould including a row of interconnected cavities defining individual teeth of said tooth portion arranged in the manner in which they are to appear in the completed arch forms, the other part of said two-part mould defining a part of said tooth portion which is to be covered by a gum portion and also defining at least one projection on said part of said tooth portion; injecting plastics material into said two-part mould thereby forming said tooth portion; withdrawing said other part of said two-part mould from said one part thereof; providing a further mould part defining said gum portion; placing said further mould part over said part of said tooth portion to be covered by said gum portion when said tooth portion is in said one part of said two part mould; injecting plastics material into said further mould part, thereby in situ moulding said gum portion onto said tooth portion so as to overlie said part thereof and surround said at least one projection; withdrawing said further mould part from said one part of said two-part mould and removing the resultant moulded arch from said one part of said two-part mould.

7. The method according to claim 6, wherein said tooth portion is injection moulded by injecting said plastics material into said two-part mould through a gate disposed substantially midway along the rear of said cavities in said one part of said two-part mould.

8. The method according to claim 6 wherein cavities in said one part of said two-part mould which define rear teeth of said tooth portion are inclined towards cavities in said one part of said two-part mould which define front teeth of said tooth portion, such that there are no undercut surfaces in said mould with respect to a predetermined direction, and said moulded tooth portion is removed from said one part of said two-part mould in said predetermined direction.

9. An arch form comprising a tooth portion including a plurality of integral teeth injection moulded in a plastics material and arranged in a row in the manner in which they are to appear in the complete arch form, front teeth of said plurality of integral teeth having a substantially natural inclination with respect to a general plane of said tooth portion, rear teeth of said plurality of integral teeth being inclined towards said front teeth such that their direction of extent is angled with respect to their counterparts in a natural set of teeth, the arch form further comprising a gum portion in situ injection moulded onto said tooth portion so as to overlie a part thereof, and at least one integral projection provided on said part of said tooth portion, said gum portion surrounding said at least one projection.

* * * * *